US006224863B1

(12) United States Patent
Bacic et al.

(10) Patent No.: US 6,224,863 B1
(45) Date of Patent: May 1, 2001

(54) ANTIBIOTIC COMPOSITION FROM ALCALIGENES SPECIES AND METHOD FOR MAKING AND USING THE SAME

(75) Inventors: Melissa K. Bacic; Duane C. Yoch, both of Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 09/201,754

(22) Filed: Dec. 1, 1998

Related U.S. Application Data
(60) Provisional application No. 60/106,430, filed on Oct. 30, 1998.

(51) Int. Cl.[7] .............................. A61K 35/74; C12P 1/04
(52) U.S. Cl. ........................................... 424/115; 435/170
(58) Field of Search .............................. 424/115; 435/170

(56) References Cited

U.S. PATENT DOCUMENTS 3,655,510    4/1972  Tanaka et al. .

FOREIGN PATENT DOCUMENTS

05078355  *  3/1993  (JP) ..................................... 424/115

OTHER PUBLICATIONS

Bizet et al., Pathol. Biol., 40(5), 591–8 Abstract Only, 1992.*
Mark P. deSouza and Duane C. Yoch, "Purification and Characterization of Dimethylsulfoniopropionate Lyase from an *Alcaligenes*–Like Dimethyl Sulfide–Producing Marine Isolate," 61:21–26, *Applied and Environmental Microbiology*, Jan. 1995.
K. Kamigiri et al, "Kalimantacins A, B and C, Novel Antibiotics from Alcaligenes sp. YL–02632S: Taxonomy, Fermentation, Isolation and Biological Properties," 49:136–139, *Journal of Antibiotics*, Feb. 1996.
T. Tokundaga, et al, "Kalimantacins A, B and C, Novel Antibiotics from Alcaligenes sp. YL–02632S: Physico–chemical Properties and Structure Elucidation," 49:140–144, *Journal of Antibiotics*, Feb. 1996.
Wratten et al., "Antibiotic Metabolites from a Marine Pseudomonad," 411–414, *Antimicrobial Agents and Chemotherapy*, vol. 11, No. 3, Mar. 1977.
Gandhi, et al., "Prodigiosin Metabolites of a Marine Pseudomonas Species," 34:223–227, *Marine Biology*, 1976.
Burkholder, et al., "Production of a Pyrrole Antibiotic by a Marine Bacterium," 14:649–653, *Applied Microbiology*, Mar. 1966.
Andersen, et al., "Autotoxic Antibiotic Production by a Marine Chromobacterium," 27:281–285, *Marine Biology*, 1974.
Jones, et al., Journal Highlights, "Novel Oxazolidinones Squash Resistant Gram–Positive Organisms," 62:261, ASM News, 1996.
Fenical, W., "Chemical Studies of Marine Bacteria: Developing A New Resource," 93:1673–1683, *Chem. Rev.* 1993.
CDC, "Drug Resistance 'Staph' Isolate with Low–Level Resistance to Vancomyacin Reported in U.S.", ISSN: 1078–2907, *Health Letter on the CDC*, Sep. 1, 1997.
Donna Leinwand, "Super Bugs Evolving in Suburbs? Middle–class Abuse of Antibiotics Cited," *The Record, Northern New Jersey*, Jan. 20, 1998.
Anita Manning, "Antibiotic–Resistant Plague Strain Found," *USA Today*, Sep. 4, 1997.
Scott F. Dowell, Benjamin Schwartz, "Resistant Pneumococci: Protecting Patients through Judicious Use of Antibiotics," *American Family Physician*, Apr. 1, 1997.
"Consumer Alert: Antibiotic Resistance is Growing!," vol. 16, No. 4, ISSN: 0736–4873, *Newsletter—People's Medical Society*, Aug. 1, 1997.
"Trend: Anti–Infectives: Survey Finds Rise in Resistant Organisms," *Applied Genetics News*, vol. 17, No. 11, Jun. 1, 1997.
"High Level Resistance to Ciprofloxacin in *Escherichia Coli*," *The Lancet*, vol. 349, No. 49, Feb. 8, 1997.
"Drug Resistance Multi–Drug Resistnat *Salmonella Typhimurium*," *Disease Weekly Plus*, Feb. 10, 1997.
"Front Page: Deadly Drug–Resistant Bacteria Gaining Ground," *Asahi Evening News*, Dec. 29, 1997.
"FDA Task Force Formed to Tackle Antibiotic Resistance Issue," *Chemical Business NewsBase*, Dec. 19, 1997.
Salvado, et al., "Drug Resistance (Mycobacteria) (beta)–Lactamases and Suseptibility to (beta)–Lactam Antibiotics in Mycobacterium fortuitum and Mycobacterium mucogenicum Strains," *Tuberculosism & Airborne Disease Weekly*, Jan. 12, 1997.
Jones, Mark E., "Widespread Occurence of Integrons Causing Multiple Antibiotic Resistance in Bacteria," *The Lancet*, vol. 349, No. 9067, Jun. 14, 1997.
"Health–Officials Fight Deadly Bacteria," *Dayton Daily News*, Jan. 18, 1998.

* cited by examiner

*Primary Examiner*—Jerome D. Goldberg
(74) *Attorney, Agent, or Firm*—Nelson Mullins Riley & Scarborough, L.L.P.

(57) ABSTRACT

A method and composition for treating a bacterial infection in humans and animals is disclosed. The composition contains an anti-bacterial agent that inhibits or kills a variety of Gram-negative and Gram-positive pathogenic bacteria, including several previously shown to be drug-resistant. In particular, the anti-bacterial agent comprises an antibiotic produced by members of the Alcaligenes genus. For instance, in one embodiment, the antibiotic is produced by the M3A strain of *Alcaligenes faecalis*. The antibiotic of the present invention can be administered parenterally or via a mucosal route.

12 Claims, 6 Drawing Sheets

ANTIBIOTIC COMPOSITION FROM ALCALIGENES SPECIES AND METHOD FOR MAKING AND USING THE SAME

This application claims the benefit of U.S. Provisional Application No. 60/106,430 filed Oct. 30, 1998.

FIELD OF THE INVENTION

The present invention is generally directed to a composition and process for treating bacterial infections. Specifically, the present invention is directed to a composition containing and use of an antibiotic produced by an *Alcaligenes faecalis* species to kill and inhibit the growth of bacteria that cause infectious diseases.

BACKGROUND OF THE INVENTION

Antibiotics (also known as antimicrobials) are chemical compounds used to kill or inhibit the growth of infectious organisms. Originally the term antibiotic referred only to organic compounds, produced by bacteria or molds, that are toxic to other microorganisms. Currently, the term now includes synthetics and semi-synthetic organic compounds.

Antibiotics generally refer to anti-bacterials, however, a loose definition may include such specific compounds as antivirals, anti-protozoals, and antifungal agents. All antibiotics share the property of selective toxicity, however, in that they are more toxic to an invading organism than they are to an animal or human host.

Antibiotics may be classified as bactericidal (bacterial-killing) or bacteriostatic (inhibiting bacterial proliferation). Bacteriostatic drugs are effective because bacteria prevented from multiplying will eventually be killed by the defense mechanisms of the host.

Antibiotics are further defined according to their mechanisms of action. For example, many antibiotics act by selectively interfering with the synthesis of bacterial constituents, such as the cell wall or bacterial nucleic acids. Beta-lactam antibiotics, which include the penicillins, interfere with the synthesis of peptidoglycan, the major component of bacteria cell walls. By interfering with peptidoglycan synthesis, material accumulates inside bacterial cells, exerting increasing pressure on the membrane. Eventually, the membrane ruptures and the cellular contents leak out, resulting in the bacterial death. Since mammalian cells do not have peptidoglycan, they are not affected by the action of penicillin-like agents.

Other antibiotics operate by inhibiting the synthesis of various intracellular bacterial molecules, including DNA, RNA, ribosomes, and protein. For example, antibiotics like Rifampicin inhibit enzymes involved with nucleic acid synthesis, such as DNA polymerase. By contrast, Quinoline antibiotics inhibit synthesis of the enzyme responsible for the coiling and uncoiling of the chromosomes, a process necessary for DNA replication and messenger RNA transcription. Still other pharmacologically-active compounds, such as the tetracyclines, compete with incoming transfer-RNA molecules.

One of the most common methods of classifying bacteria is based upon differential staining characteristics, using a procedure such as the Gram's stain. Some species of bacteria have a cell wall consisting primarily of a thick layer of peptidoglycan. Other species have a much thinner layer of peptidoglycan and an outer, as well as an inner, membrane. When bacteria are subjected to a Gram's stain, the differences in cell wall structure produce differential staining of the bacteria. Bacteria classified as Gram-positive organisms appear purple, while those classified as Gram-negative appear reddish.

Antibacterial drugs can also be classified according to those which are effective against Gram-positive bacteria; those with activity against Gram-negative bacteria; and those agents effective against members of both Gram-positive and Gram-negative classifications. For example, the penicillins are classified as narrow-spectrum antibiotics, with activity against many Gram-positive bacteria. The tetracyclines and chloramphenicols are classified as broad spectrum drugs because they are effective against both Gram-positive and Gram-negative bacteria.

Originally, antibiotics were primarily isolated from bacteria or from molds. Penicillin, for example, was derived from the mold *Penicillium chrysogenum*. The effectiveness of Penicillin as an antibiotic was accidentally discovered in 1928 by Sir Alexander Fleming, who showed its efficacy in laboratory cultures against many disease-producing bacteria. Fleming's discovery marked the beginning of the development of antibacterial compounds produced by living organisms.

Other antibiotics have been isolated from a group of soil bacteria, called actinomycetes. One of these, streptomycin, was discovered in 1944 by Selman Waksman and his colleagues. Streptomycin was originally the primary chemotherapeutic agent used against tuberculosis. The management of infectious diseases has been transformed by the use of antibiotics. The incidence of many diseases once responsible for high mortality and morbidity, such as tuberculosis, pneumonia, and bacterial meningitis, has been reduced because of successful antibiotic treatment. Indeed, a whole branch of pharmacology has been devoted to the discovery and development of synthetic antibiotics, which exhibit increased efficacy and safety for the treatment of infectious organisms.

However, the increased use of antibiotic therapy has been accompanied with a corresponding increase in the evolution of bacterial defenses against the drugs. One of the main defense mechanisms used by bacteria is the inactivation of the antibiotic molecule. This mechanism is one of the bases of bacterial resistance against both penicillin and chloramphenicol, among others.

Another bacterial defense involves a mutation which changes a bacterial enzyme, such that the antibiotic no longer effectively inhibits the bacterial growth. This is the main mechanism of resistance to compounds that inhibit protein synthesis, such as the tetracyclines.

Of even greater concern is that many mechanisms resulting in antibiotic resistance are transmitted genetically from the bacterium to its progeny. Genes that carry resistance can also be transmitted from one bacterium to another by means of plasmids (extrachromosomal pieces of DNA). Because plasmids are easily acquired and lost by bacteria, drug resistance may spread rapidly among bacterial species.

Plasmids have also been identified which carry resistance to several different classes of antibiotics, thus creating bacteria resistant to all attempts at drug therapy. For example, a strain of bubonic plague has been found recently which is resistant to multiple antibiotics.

The danger inherent in emerging drug resistance is exemplified in the disease tuberculosis In the 1970's, tuberculosis appeared to have been nearly eradicated in the United States and other developed countries. Now, its incidence is increasing at an alarming rate, partly due to the emergence of an antibiotic resistant strain.

Currently, antibiotic resistance in bacteria has reached a crisis point in healthcare, with the discovery of many bacterial isolates which display multi-drug resistance to many of the known antimicrobials. A study jointly supported by the State University of New York (Buffalo) and the University of Iowa College of Medicine analyzed over 17,000 bacterial isolates associated with hospital-acquired (nosocomial) infections, obtained from 215 medical sites across the country. Results of this study showed a sharp increase in the occurrence of antibiotic resistance among bacterial isolates.

Recent studies have shown an increase in Methicillin resistant strains of *Staphylococcus aureus* (MRSA), which can cause boils, pneumonia, and toxic shock. Currently, approximately 30% of the *S. aureus* strains isolated exhibit drug resistance. Further, in May of 1997, the Centers for Disease Control and Prevention (CDC) reported isolation of an *S. aureus* strain which had developed resistance to Vancomycin, one of the most powerful antibiotics currently available. Because *S. aureus* is the most frequent cause of nosocomial infections, this discovery alarmed healthcare workers and infectious disease specialists.

The list of resistant organisms is increasing daily. Between 1988 and 1996, researchers observed an approximately 50-fold increase in the number of Vancomycin-resistant Enterococcus strains isolated from clinical samples. Enterococcus, which can cause meningitis, heart inflammation, and stomach infections, most often affects the elderly and those with a weakened immune system. Thus, the acquistion of Vancomycin-resistance greatly concerns public health officials, as they seek to develop methods to control a potentially fatal bacterium before its resistance spreads to even deadlier organisms.

The increase in drug resistance among medically important bacteria has led to an interest in the development of novel drug candidates, especially those with efficacy against multiple drug resistant (MDR) infectious agents. Over the past 60 years, between 30,000 and 50,000 natural products have been derived from microorganisms, mainly soil-derived bacteria and fungi. More than 10,000 of these compounds are biologically active, the majority of which are antibiotics and anti-tumor agents. Although soil bacteria continue to be studied extensively, with the goal of discovering other novel anti-bacterial agents, it is clear that the rate of discovery for novel antibacterial agents is decreasing. Therefore, scientists have begun to evaluate new sources of bioactive natural products, in hopes of discovering other effective pharmacologically-active agents.

Oceans compose over 70% of the earth's surface and over 90% of the volume of its crust. Microbiologically, the oceans are massively complex and contain a diverse group of lifeforms. Indeed, marine microorganisms have developed unique physiological capabilities to survive in an environment of extreme variation in pressure, salinity, and temperature. Thus, these microorganisms offer the potential for the production of metabolites which may not be observed in the more familiar soil-derived microorganisms.

Previously, microorganisms isolated from seawater have been shown to produce compounds and metabolites with effective antibiotic activity. The first such molecules to be isolated were highly brominated pyrroles, but these compounds were not effective against Gram-negative bacteria. However, tetrabromopyrrole, isolated from a marine organism of the Altermonas genus, was shown to be effective against other marine bacteria.

Other investigators found that certain marine pseudomonads also produce antibiotics, such as 2-n-pentylquinolinol, which exhibits activity against *Vibrio harveyi*. Similarly, a Pseudomonas species isolated from tropical green algae produces two antibiotic "pigments," known as magnesidins. Finally, a seawater-derived bacterium of unknown identity was found to produce a new lactone, oncorhynoclide, which inhibited various test organisms.

Microbes isolated from marine sediments have also been shown to produce pharmacologically-active antibiotics, and almost all of these organisms belong to the Order Actinomycetales. Many antibiotic-producing terrestrial strains also belong to this Order, of which the genus Streptomyces is the best known member. Common antibiotics like Chloramphenicol, Novobiocin, and Bacitracin also were originally derived from terrestrial microorganisms.

Currently, scientists are examining other marine and terrestrial species to identify novel compounds which exhibit antibiotic activity. Because of the alarming increase in drug resistance already noted, there is a pressing need for the development of such novel antimicrobials, especially those exhibiting efficacy against multiple drug-resistant organisms.

SUMMARY OF THE INVENTION

The present invention recognizes and addresses the foregoing disadvantages, and others of prior art constructions and methods.

In summary, the present invention is generally directed to a novel antibiotic elaborated by a marine organism, that can be used to destroy and inhibit the growth of clinically important bacteria, especially those strains which have previously been shown to be resistant to common antimicrobial agents. The antibiotic of the present invention is produced by a bacterium classified biochemically as belonging to the genus Alcaligenes. Results of fatty acid analysis and 16S ribosomal typing have assigned the organism to the species *faecalis*. The inventors have further designated this strain of *A. faecalis* as M3A.

The inventors have discovered that the antibiotic elaborated by the M3A strain of *A. faecalis* unexpectedly inhibits both Gram-negative and Gram-positive bacteria, including clinically-relevant isolates shown to be resistant to other antimicrobials. Efficacy against multi-drug resistance bacterial strains (MDR) make the antibiotic of the present invention a highly effective and desirous agent for treating infectious agents.

Isolation of the *A. faecalis* M3A marine strain was previously described in a publication entitled "Purification and Characterization of Dimethylsulfoniopropionate Lyase from an Alcaligenes-Like Dimethyl Sulfide-Producing Marine Isolate," Mark P. deSouza and Duane C. Yoch, Applied and Environmental Microbiology, 61:21–26 (January 1995). The isolation procedure and biochemical characteristics of *A. faecalis* M3A are described in Examples 1 and 3, and a sample of the strain has been deposited with American Type Culture Collection (Accession No. ATCC 700596; deposit date: Aug. 7, 1998). However, it was not disclosed in the deSouza and Yoch publication, nor was it apparent based on that publication, that the M3A strain produced an antibiotic factor.

Accordingly, it is an object of the present invention to provide a method and a composition for treating infectious diseases.

Another object of the present invention is to provide an antibiotic composition and a method for using the same.

Still yet another object of the present invention is to provide an antibiotic composition produced by marine bacteria useful for inhibiting and destroying the growth of medically important bacteria.

A further object of the present invention is to provide a pharmacologically active preparation that contains an antibiotic produced by Alcaligenes species.

Still another object of the present invention is to provide an antibiotic composition for inhibiting and destroying the growth of multi-drug resistant bacteria.

These and other objects of the present invention are achieved by providing an antibiotic composition and method for treating a bacterial infection in human or animal patients. The process includes the step of treating a human or animal patient with an effective amount of the antibiotic produced by Alcaligenes to inhibit or destroy the bacteria responsible for causing the infection. Specifically, the antibiotic is capable of inhibiting the growth of *Escherichia coli, Pseudomonas aeruginosa, Mycobacterium avium, Mycobacterium tuberculosis,* and Enterococci, as well as other bacterial species shown to be resistant to traditional antibiotic therapy. In one embodiment, an antibiotic produced by the M3A strain of *Alcaligenes faecalis* is used.

The antibiotic composition of the present invention may be used to treat infectious bacteria alone or in conjunction with other pharmaceutical agents. Besides containing the antibiotic produced by *Alcaligenes faecalis* M3A, the composition can contain other antimicrobial agents, wetting agents, carriers, emulsifying agents and the like, depending upon the type of administration and the preparation desired. Other objects, features and aspects of the present invention are discussed in greater detail below.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying Figures, in which.

DETAILED DESCRIPTION OF THE PREFERRED EMBODIMENT

Figure 1:
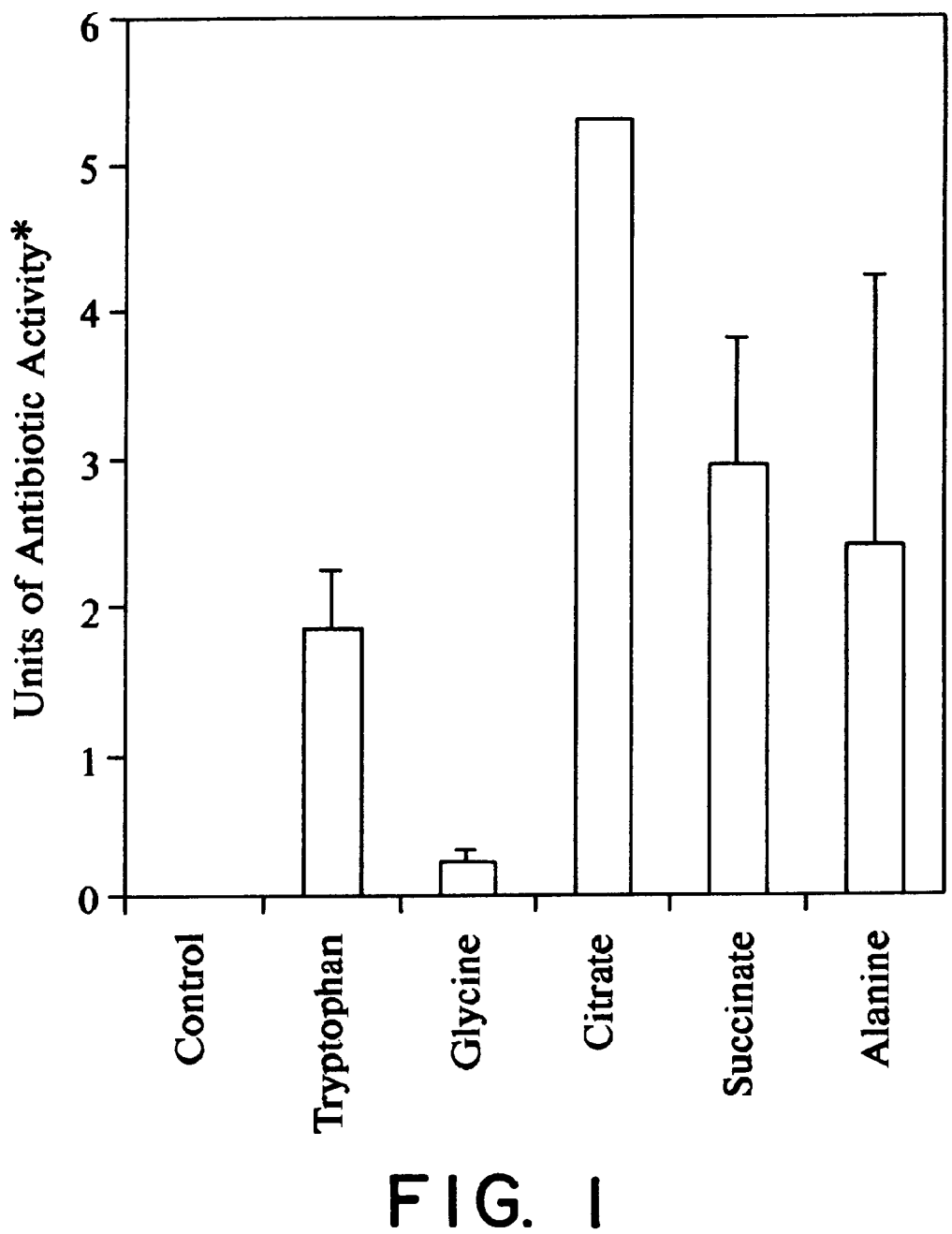
FIG. 1 is a bar graph depicting the results of an experiment assessing the effect of different carbon sources in the media on M3A antibiotic activity.

It is to be understood by one of ordinary skill in the art that the present discussion is a description of exemplary embodiments only, and is not intended as limiting the broader aspects of the present invention, which broader aspects are embodied in the exemplary constructions.

The present invention is generally directed to a composition and process for treating bacterial infections in human and animal patients. The process is directed to administering to a patient a composition containing an antibiotic isolated and purified from Alcaligenes bacterial cultures. Specifically, in one embodiment, an antibiotic derived from the M3A strain of *Alcaligenes faecalis* cultures is administered to inhibit the growth of clinically relevant bacterial test cultures. In particular, it has been discovered that the antibiotic produced by strain M3A of *A. faecalis* effectively inhibits the growth of *Escherichia coli, Pseudomonas aeruginosa,* and other medically important bacteria shown to be resistant to treatment with traditional antibiotics.

The antibiotic composition from Alcaligenes can be administered in dosages and by techniques well-known to those skilled in the medical or veterinary arts, taking into consideration such factors as the age, sex, weight, species and condition of the particular patient, and the route of administration.

The route of administration can be percutaneous, via mucosal administration (e.g., oral, nasal, anal, vaginal), or via a parenteral route (intradermal, intramuscular, subcutaneous, intravenous, or intraperitoneal). The M3A antibiotic can be administered alone, or can be co-administered or sequentially administered with other treatments or therapy. Forms of administration may include suspensions, syrups or elixirs, and preparations for parenteral, subcutaneous, intradermal, intramuscular, or intravenous administration (e.g., injectable administration), such as sterile suspensions or emulsions. The parenteral antibiotic may be administered in admixture with a suitable carrier, diluent, or excipient such as sterile water, physiological saline, glucose, dextrose, or the like. The compositions can contain auxiliary substances such as wetting or emulsifying agents, pH buffering agents, adjuvants, gelling, or viscosity enhancing additives, preservatives, flavoring agents, colors, and the like, depending upon the route of administration and the preparation desired. Standard pharmaceutical textbooks, such as "REMINGTON'S PHARMACEUTICAL SCIENCE," 17th Edition, 1985, may be consulted to prepare suitable preparations, without undue experimentation.

As mentioned above, the effective dosage and route of administration are determined by the therapeutic range and nature of the compound, and by known factors such as the age, weight, and condition of the host, as well as the $LD_{50}$ and other screening procedures which are known to those in the art, and do not require undue experimentation. Dosages can generally range from a few hundred micrograms to a few grams.

It has previously been shown that at least one other strain of Alcaligenes is an antibiotic-producer, as described in two publications entitled "Kalimantacins A, B and C, Novel Antibiotics from Alcaligenes sp. YL-02632S: Taxonomy, Fermentation, Isolation and Biological Properties," K.

Kamigiri et al, *Journal of Antibiotics*, 49: 136–139 (February 1996) and "Kalimantacins A, B and C, Novel Antibiotics from Alcaligenes sp. YL-02632S: Physicochemical Properties and Structure Elucidation," T. Tokunaga et al, *Journal of Antibiotics*, 49:140–144 (February 1996) respectively. However, it is believed the antibiotics produced by Alcaligenes sp. YL-02632S are not the same as in the present invention, since kalimantacins A, B and C are insoluble in water, but soluble in organic solvents. In contrast, the M3A antibiotic is soluble in water, but insoluble in organic solvents.

Further, the antibiotic of the present invention is believed to be particularly effective at inhibiting the growth of, and destroying, many of the clinically important bacterial isolates known to exhibit resistance against traditional antimicrobials. For example, the M3A antibiotic has been shown to be effective at inhibiting the growth of, and destroying, multi-drug resistant (MDR) isolates of *Escherichia coli*, *Pseudomonas aeruginosa*, and *Mycobacterium tuberculosis*, among others, while the activity of kalimantacins A, B and C is apparently only effective against strains of *Staphylococcus aureus* and *S. epidermidis*.

The present invention may be better understood with reference to the following examples, said examples which are meant to be exemplary procedures only, to aid in the understanding of the present invention, and not meant to serve as limitations thereof.

EXAMPLE 1

Strain M3A Isolation

Salt marsh sediment (30 g) from the bank of Shem Creek in Charleston Harbor was vortexed with an equal volume of filtered (pore size, $0.22\mu$) seawater and allowed to settle. The supernatent was used to inoculate a minimal medium containing acrylate as a carbon-energy source. The basal medium contained the following (per liter): 10 ml of basal salts solution ($MgSO_4.7H_2O$, 20 g liter$^{-1}$; $CaCl_2.2H_2O$, 7.5 g liter$^{-1}$; Fe-EDTA [Sigma], 2.95 g liter$^{-1}$; 10 ml of trace elements [$MnSO_4$, 15.99 g liter$^{-1}$; $H_3BO_3$, 28 g liter$^{-1}$; $CuSO_4.5H_2O$, 0.79 g liter$^{-1}$; $ZnSO_4.7H_2O$, 2.4 g liter$_{-1}$; $Na_2MoO_4.2H_2O$, 12.6 liter$^{-1}$;]); $(NH_4)_2SO_4$, 0.66 g; NaCl, 1.17 yeast extract, 0.05 g; acrylic acid, 0.34 ml of a 100% solution or 5 mM final concentration. This medium was supplemented with 1 ml of a vitamin mixture containing vitamin $B_{12}$ (2 mg liter$^{-1}$) and the following at 10 mg liter$^{-1}$: p-aminobenzoic acid, riboflavin, vitamin $B_6$, niacin, vitamin C, thiamine, and D-(+)-biotin. The vitamin solution was autoclaved and stored refrigerated. The pH of the medium was adjusted to 6.4 prior to autoclaving. Phosphate buffer (1 M; pH 6.8; $KH_2PO_4$ [60 g liter$^{-1}$] plus $K_2HPO_4$ [90 g liter$^{-1}$]) at 10 ml liter$^{-1}$ was autoclaved separately and added after the medium had cooled; the final pH of the medium was 7.0.

After 72 hours, the culture was streaked on petrie plates containing the acrylate medium described above. After incubation for a week at 30° C., numerous colonies appeared and were restreaked onto separate plates to obtain pure cultures. These cultures were washed off the plates with 50 mM phosphate buffer (pH 7.0) and assayed for dimethylsulfoniopropionate (DMSP) lyase activity. The M3A isolate was chosen among the several cultured because it grew rapidly on acrylate under aerobic conditions, attaining a cell density of 0.6 to 0.8 ($A_{420}$) in a 9-liter batch culture within 72 hours. Strain M3A also exhibited high rates of DMSP lyase activity.

EXAMPLE 2

Spent Medium Preparation for Optimal Antibiotic Activity

Strain M3A was streaked for isolation onto a Trypticase Soy agar (TSA) plate and allowed to grow. A single colony from this plate was inoculated into 250 mls of Mel's Citrate Minimal Medium (MCMM); which contains the following (per liter): $NaNH_4HPO_4.4H_2O$: 1.05 gm; $Na_3C_6H_5O_7.2H_2O$: 1.47 gm; and $K_2HPO_4$: 0.87 gm in distilled water. The solution was adjusted to a final pH of 7.0, with the addition of either KOH or HCl; autoclaved; and supplemented with sterile salts to a final concentration as follows: $MgSO_4$: 0.12 gm/L; $CaCl_2$: 0.011 gm/L; and $FeSO_4$: 0.0028 gm/L.

Following inoculation with strain M3A, media aliquots were incubated in a shaker at 30 degrees C., until a cell density of 170–200 units was reached, as measured by a Klett photoelectric colorimeter (Manostat). The media was then harvested by centrifugation, the supernatant was filter-sterilized ($0.2\mu$ pore-size filter), heated to 85 degrees C. for 10 min, and stored at 4 degrees C. until use.

To test the inhibitory ability of the M3A antibiotic, spent medium was inoculated with a test bacterial strain and the ability of the antibiotic to inhibit growth of the test organism assessed. Unless otherwise noted, *Staphylococcus aureus* (ATCC strain 12600) was used as the test strain, and prepared by inoculating half-strength Tryptic Soy Broth (TSB) with a single colony of *S. aureus*. The cultures were allowed to grow overnight, or until a cell density of about 500 Klett units was reached. Three ml of *S. aureus* culture (or other test culture) was added to each ml of spent medium to assess inhibitory ability of the M3A antibiotic.

EXAMPLE 3

Morphological, Physical and Biochemical Characteristics of Strain M3A and its Antibiotic Morphological Characteristics Strain M3A is a gram-negative, rod-shaped bacterium and a facultative anaerobe. The isolate grows well on Tryptic Soy agar (TSA) plates, with resulting colonies producing a diffusible, yellow, non-fluorescent pigment.

Physical Characteristics

The M3A antibiotic appears to be very stable to changes in either pH or temperature. Spent medium, prepared as described in Example 2, was treated with HCl (1M) or NaOH (1M) and then tested to determine the antibiotic's inhibitory ability against the growth of *S. aureus*. Results showed that the M3A antibiotic was unaffected either by lowering the pH to 3.0 for 30 minutes, or by raising the pH to 12 for 30 minutes.

In a separate experiment, the antibiotic was heated to 85° C. for 10 minutes. Results showed that such heating did not affect the ability of the antibiotic to inhibit the growth of the *S. aureus* test culture. However, either boiling or autoclaving the spent media for 10 minutes slightly reduced the antibiotic's inhibitory action on the *S. aureus* culture.

In other experiments, the effect of proteinases on the M3A antibiotic was examined. Spent medium from M3A cultures, or from a non-antibiotic producing control organism, was incubated with either trypsin or proteinase K for thirty minutes, after which the proteinase was inactivated (by the addition of fetal bovine serum in the case of trypsin or EDTA in the case of proteinase K). Nutrients (yeast extract, peptone and salts) were added to the cultures containing EDTA, and all cultures were inoculated with the test organism. Results showed that neither proteinase k nor trypsin treatment reduced the ability of the M3A antibiotic to inhibit *S. aureus* growth, thus suggesting the M3A antibiotic is neither a large molecule or a protein.

Additional experiments were performed to determine other physical characteristics of the M3A antibiotic molecule. For example, spent medium was subjected to anion (DEAE Cellulose; Sigma Chemicals) and cation (AG 50W-X8, Bio Rad) exchange chromatography. Since the antibiotic bound only to the cation exchange column, results suggest the presence of positively-charged groups. The elution profile indicates these groups could be $NH_3$ moieties.

Gel filtration chromatography (G-10 Sephadex, Pharmacia), using a K-ferricyanide standard (molecular weight of 329.3), showed the M3A antibiotic came off the column immediately behind the standard, indicating a molecular weight of approximately 300.

Toxicity testing was also conducted. Spent medium was lyophilized, rehydrated, and passed through a Sephadex G-10 desalting column. Fractions were collected and tested for inhibitory activity on a *S. aureus* lawn. Fractions shown to inhibit *S. aureus* were used subsequently to inject DBA/BL6 mice (mean weight of 29.5 gm). Each mouse was injected subcutaneously (100 ml/mouse), while controls were injected with saline, distilled water, or column fractions lacking inhibitory activity. Results showed that all mice were alive and thriving 5 days post-injection.

In another set of experiments, 26 BALB/c mice were injected intraperitoneally with spent medium concentrated 25, 50, or 100 times. Eleven controls received equally-concentrated spent medium prepared from Enterobacter cultures. Results showed all mice survived and were thriving one week post-injection.

Biochemical Characteristics

The M3A strain was characterized biochemically using a commercial Vitek gram-negative Identification Card system (Vitek). Results of the Vitek panel identified the isolate with 95% certainty as a member of Alcaligenes genus. However, the M3A isolate differed from known Alcaligenes species in several key characteristics, including colony morphology, production of a diffusible pigment, and growth on certain carbon sources. Therefore, M3A was characterized as an Alcaligenes-like species.

Ribosomal RNA sequencing was also performed. Results revealed that M3A shares greater than 98.9% identity with *Alcaligenes faecalis*, a ubiquitous organism, which has not previously been identified as producing an antibiotic. However, the M3A strain also differs from known *A. faecalis* strains, as seen when the growth of the M3A isolate is compared to that of the *A. faecalis*-type strain available from the American Type Culture Collection. The following table compares the growth of the two strains on various substrates:

| SUBSTRATE | M3A | A. Faecalis (ATCC) |
| --- | --- | --- |
| Formate | − | +/− |
| Acetate | + | + |
| Propionate | + | + |
| Succinate | + | + |
| Fumarate | + | + |
| D-malate | + | − |
| Lactate | + | + |
| Pyruvate | + | + |
| Glycerol | − | − |
| Glucose | − | − |
| Sucrose | − | − |
| D-mannitol | − | − |
| D-ribose | − | − |
| D-gluconate | − | − |
| Citrate | + | + |
| D-fructose | + | − |
| D-arabinose | − | − |
| Lactose | − | − |
| Butyrate | + | + |
| Glycine | + | + |
| L-glutamate | − | − |
| Hydroxybenzoate | + | − |
| Acrylate | + | − |
| DMSP | + | − |
| Sorbitol | − | − |
| Maltose | − | − |

Additional morphological and biochemical characteristics of the M3A isolate are summarized as follows:

| Characteristic | Value or Description |
| --- | --- |
| Morphology | Short rods in pairs |
| Flagellar arrangement | peritrichous |
| Cell length ($\mu$m) | 1 |
| Cell width ($\mu$m) | 0.6 |
| Gram reaction | Negative |
| Motility | + |
| Colony type | Dimorphic-punctate and diffuse |
| Soluble pigment production | + (yellow, nonfluorescent) |
| Oxidase | + |
| Catalase | + |
| Citrate | + |
| Aerobic acid production from: | |
| Maltose | + |
| Mannitol | − |
| Xylose | + |
| L-Arabinose (fermentative) | + |
| Growth on acetate | + |
| Growth on p-hydroxybenzoate | + |
| Growth on D-malate | + |
| Growth on D-fructose | + |
| $NO_3$ as an N source | + |
| Arginine dihydrolase | Variable |
| Action on blood | Green to brown |
| Oxygen requirement | Facultative anaerobe |

[a]The following tests were negative: lysine and ornithine decarboxylase; tryptophan; indol; malonate; DP300 (glucose fermentation in the presence of trichloro-2'-hyroxy-diphenyl ether); p-coumaric acid; acetamide; urea; nitrogenase; gelatinase; amylase; polymyxin B resistance; $H_2S$ production; fermentation of raffinose, sorbitol, sucrose, inositol, adonitol, rhamnose, o-nitrophenyl-β-D galactopyranoside, and esculin; and aerobic acid production from glucose and lactose.

EXAMPLE 4

Optimum Production of Antibiotic from M3A Bacteria

To determine conditions for optimal antibiotic production, M3A was inoculated into a basal salts medium supplemented with 10 mM of one of several carbon sources. After 24 hours of growth, spent media was harvested, filter sterilized (0.2$\mu$ filter size), supplemented with 0.1% yeast extract and 0.1% peptone, and inoculated with *S. aureus* as a test culture. Results were determined by assessing growth of the test organism in spent media containing the various carbon sources, as compared to control cultures containing 0.1% yeast extract and 0.1% peptone alone. As shown in FIG. 1, antibiotic activity was present only when M3A was cultured in media containing either tryptophan, glycine, citrate, succinate, or alanine as the source of carbon. The highest amount of antibiotic activity was seen in cultures containing citrate.

Additional experiments were conducted to determine the effect of varying the carbon source in the M3A media on the inhibition of both Gram negative and Gram positive test cultures. M3A was grown in a basal medium containing 5 mM $NaNH_4HPO_4 \cdot 4H_2O$; 5 mM $K_2HPO_4$; 1 mM $MgSO_4$; 0.1 mM $CaCl_2$; 0.01 mM $FeSO_4$; and 5 mM of a carbon source. After 18 hours of growth, 25 ml of M3A spent medium was collected and tested against both Gram-negative and Gram-positive isolates to assess inhibition of bacterial growth. Results are summarized as follows:

| Carbon Source | Inhibition of E. coli and P. aeruginosa (Gram−) | Inhibition of S. aureus and B. subtilis (Gram+) |
|---|---|---|
| Citrate | positive | positive |
| Fructose | negative | negative |
| Sucrose | negative | negative |
| Succinate | positive | positive |
| Glucose | negative | negative |
| Glutamate | negative | negative |
| Malate | negative | negative |
| Mannitol | negative | negative |
| Lactose | negative | negative |
| Lactic Acid | negative | negative |
| Arabinose | negative | negative |
| Glycine | negative | negative |
| Acetate | negative | negative |

Results of this experiment show that the described antibiotic, with activity against both Gram-positive and Gram-negative organisms, was produced only when M3A was grown in media containing citrate or succinate as the sole carbon source.

Figure 2:
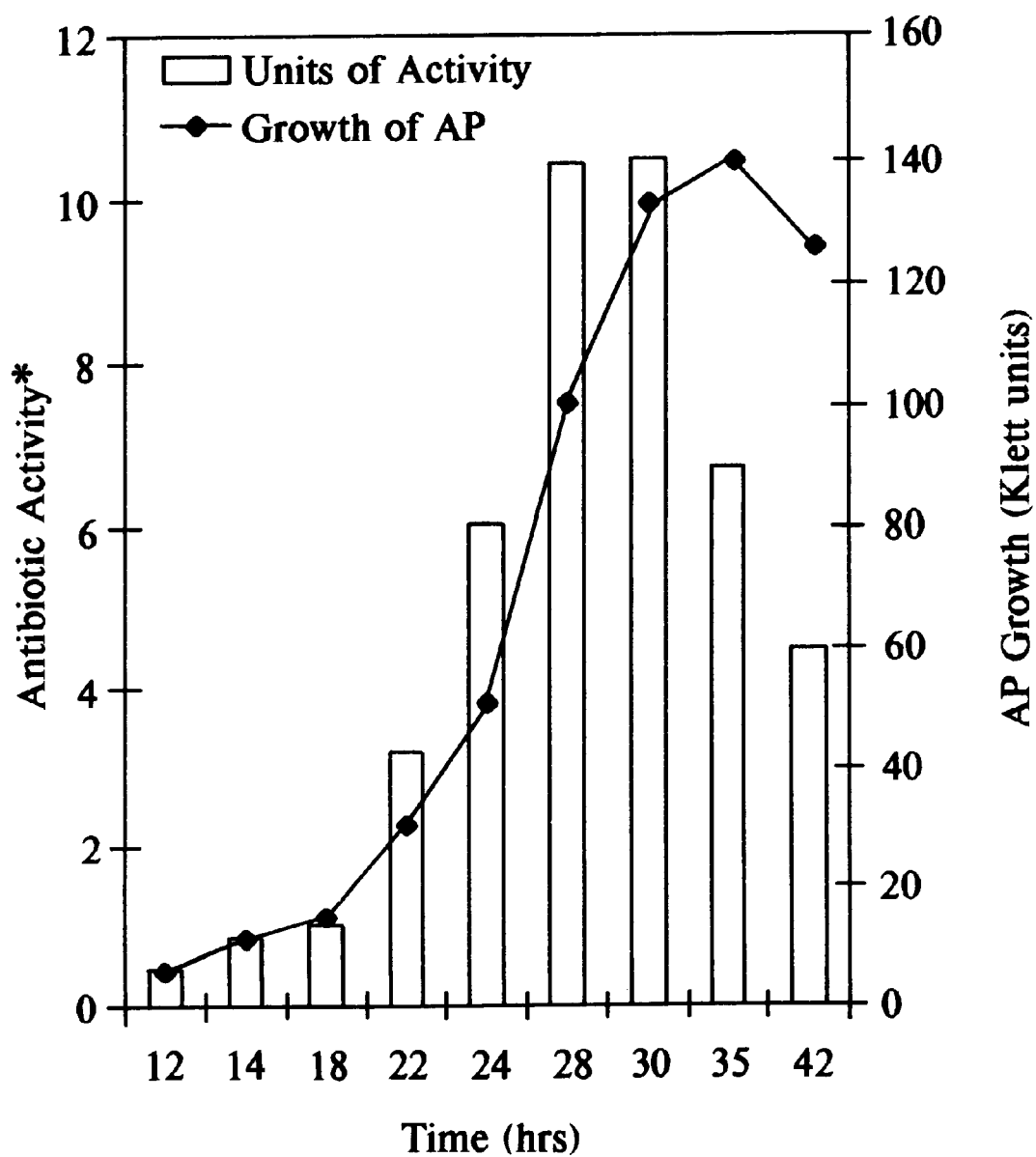
FIG. 2 is a bar graph showing the inhibition of a *Staphylococcus aureus* test culture by the M3A antibiotic in spent media, harvested from 12 to 42 hours after culture.

Experiments were also performed to examine antibiotic production as a function of the growth phase of the M3A isolate. M3A was inoculated into MCMM and an aliquot of spent medium harvested at various time points to determine ability of the M3A antibiotic to inhibit S. aureus, as described in Example 2 above. As shown in FIG. 2, the antibiotic's inhibitory activity was greatest with spent media harvested between 28–30 hours of growth (during late log phase of the M3A culture).

In a separate experiment, the inhibitory ability of the M3A antibiotic produced over a 10-day culture interval was also determined. Following inoculation of M3A into MCMM, aliquots of spent media were harvested at daily intervals and inhibition against S. aureus test organisms assessed, as described above.

Figure 3:
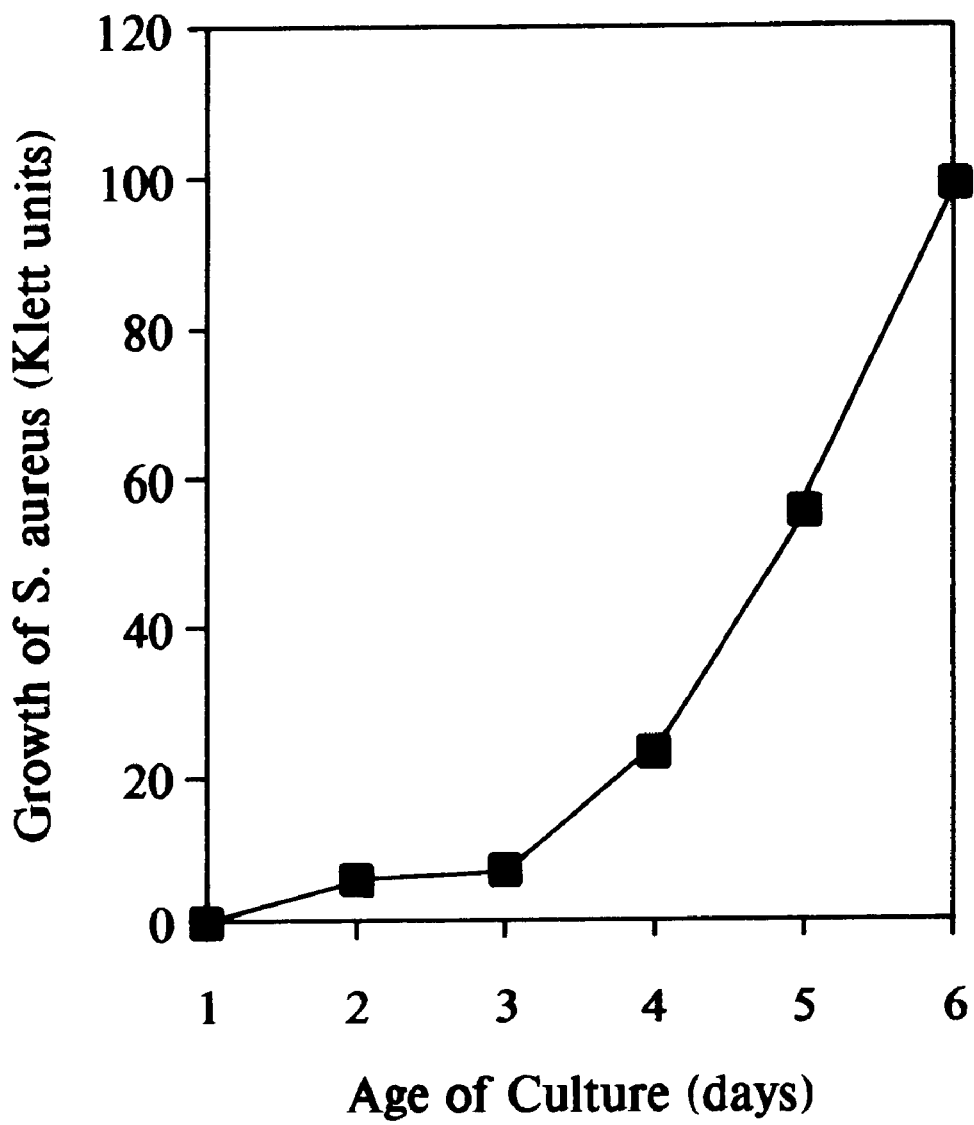
FIG. 3 is a graph showing the inhibition of the *S. aureus* test culture by the M3A antibiotic in spent media, harvested at daily intervals.

FIG. 3 graphically depicts inhibition of the S. aureus test culture by spent media containing the M3A antibiotic. The ability of the S. aureus test culture to replicate was measured using a Klett photoelectric colorimeter, which provides a measure of cell growth based on increasing turbidity. Results showed: (1) the ability of the S. aureus cultures to grow in the presence of the spent media was inversely proportional to the amount of M3A antibiotic present, and (2) the greatest amount of antibiotic activity occurred in cultures obtained from the first 24 hours of M3A incubation.

To determine the optimum temperature for antibiotic production, a similar study was conducted using M3A cultures grown in MCMM, and incubated 18–20 hours at various temperatures (17, 22, 30, 37, and 43 degrees C.). Results showed that M3A cultures incubated at 30° C. exhibited the greatest amount of antibiotic activity.

EXAMPLE 5

Inhibition of Bacterial Growth Due to Antilbiotic Production by Strain M3A

A 10 mm band of strain M3A was streaked at the base of a petri dish containing 22 ml of Tryptic Soy agar (TSA) and allowed to grow 18 hours at 30 degrees C., under aerobic conditions. Test bacterial isolates were then streaked perpendicularly to M3A, leaving a 4 mm uninoculated zone between the test organisms and M3A. Test isolates included strains of clinically relevant bacteria (Staphylococcus aureus, Streptococcus pyogenes, Pseudomonas aeruginosa, Escherichia coli, Micrococcus luteus and Streptococcus salivarius), and several different isolates of Escherichia coli, each exhibiting different antibiotic resistance (ampicillin, chloramphenicol, kanamycin, tetracycline or gentamicin resistance, respectively). The efficacy of the M3A antibiotic was also tested against several marine bacterial strains.

Results of this experiment were assessed by measuring (in millimeters) the zone of inhibition occurring when the test organism was incubated in the presence of strain M3A. The experiment showed: (1) the antibiotic produced by M3A is excreted, since it is able to diffuse a distance into the surrounding medium to inhibit the growth of the test organisms; (2) the antibiotic produced by M3A is not ampicillin, chloramphenicol; kanamycin; tetracycline; or gentamicin, since it was able to inhibit E. coli strains individually resistant to each of these drugs; and (3) the level of inhibition resulting from the action of the M3A antibiotic upon the test isolates was significant, as summarized below:

|  | Inhibition Level* |
|---|---|
| Clinically Relevant Test Isolates |  |
| Staphylococcus aureus | +++ |
| Streptococcus pyogenes (ATCC 12344) | ++++ |
| Pseudomonas aeruginosa (ATCC 27853) | +++ |
| Escherichia coli (ATCC 9637) | ++++ |
| Micrococcus luteus (ATCC 10240) | ++ |
| Streptococcus salivarius (ATCC 13419) | +++ |
| Drug Resistant Strains of E. coli |  |
| E. coli Tn5-($Ap^R Cm^R TC^R Km^R$)*** | +++ |
| E. coli pMOB-3 ($Km^R Cm^R$) | ++++ |
| E. coli pACYC-Gm ($Gm^R TC^R$) | ++++ |
| E. coli pUCGm-1 ($Gm^R AP^R$) | ++++ |
| E. coli pHP45TcΩ ($TC^R$) | ++++ |
| E. coli pZ1918 ($AP^R$) | ++++ |
| Marine Strains |  |
| Pseudomonas doudoroffii | ++ |
| Vibrio cholerae | ++ |
| V. damsela | ++ |
| V. harvii | + |
| V. natriegens | + |
| V. vulnificus | ++ |

*"+" indicates 1–5 mm of inhibition, "++" 5–10 mm, "+++" 10–20 mm, and "++++" >20 mm of inhibition.
**Ap: ampicillin, Cm: chloramphenicol, Km: kanamycin, Tc: tetracycline, Gm: gentamicin Several other drug resistant bacterial strains were tested in spent media assays. Results showed all were sensitive to the M3A antibiotic. The additional strains tested are summarized as follows:

| ORGANISM | RESISTANT TO: |
|---|---|
| Pseudomonas 19801* | Ak, Ap, Aug, Cph, Cld, Er, Gm, Neo, Trb, Cb |
| P. aeruginosa 19661 | Ap, Aug, Cph, Cm, Cld, Er, Pcn, Tc, Trb, Trs |
| Proteus 19806 | Ap, Aug, Cph, Cm, Cld, Er, Gm, Neo, Pcn, Tc, Tmt, Trb, Trs, Cb, PxB |
| Proteus 19661 | Ap, Aug, Cph, Cm, Cld, Er, Gm, Neo, Pcn, Tc, Trb, Trs |

| ORGANISM | RESISTANT TO: |
|---|---|
| S. aureus | macrolides, novobiocin, Tc, Sm |
| E. coli 9313 | Su, Sm, Cm, Km |

*American Type Culture Collection isolate identifier.
Ak: Amikacin;
Ap: Ampicillin;
Aug: Augmentin;
Cb: Carbenicillin;
Cph: Cephalothin;
Cm: Chlorampheniciol;
Cld: Clindamycin;
Er: Erythromycin;
Gm: Gentamicin;
Km: Kanamycin;
Neo: Neomycin;
Pcn: Penicillin;
PxB: Polymyxin B;
Sm: Streptomycin;
Su: Sulfanilamide;
Tc: Tetracycline;
Tmt: Timentin;
Trb: Tribrissen,
Trs: triple Sulfa.

EXAMPLE 6

Inhibition of E. coli by the M3A Antibiotic

TSA agar plates were inoculated with a test strain of E. coli exhibiting multiple drug resistance to ampicillin, chloramphenicol, tetracycline and kanamycin. The bacterial lawn was created by spreading the agar plate with the desired bacterial isolate and incubating overnight. A piece of filter paper, on which an overnight culture of M3A was growing, was placed in the center of the bacterial lawn containing the test strain, allowing the M3A antibiotic to diffuse into the surrounding environment.

Figure 4A:
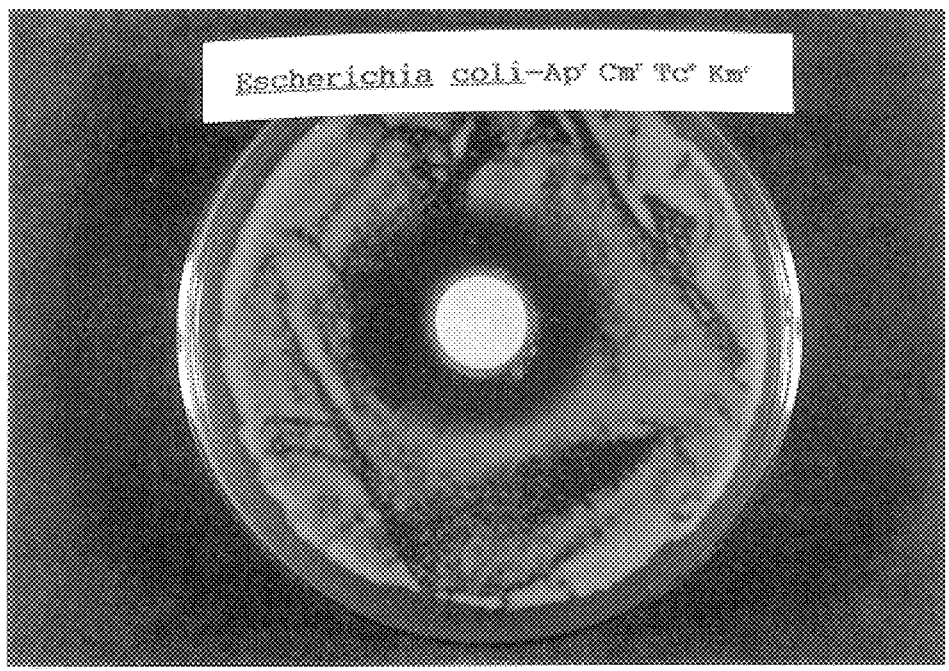
FIG. 4A is a photograph demonstrating the inhibition of a multi-drug resistant (MDR) isolate of *Escherichia coli* by the M3A antibiotic.
Figure 4B:
FIG. 4B is a photograph which demonstrates the inhibition of a gentamicin-resistant strain of *Pseudomonas aeruginosa* by the M3A antibiotic.

FIG. 4A is a photograph demonstrating M3A antibiotic inhibition of a multi-drug resistant (MDR) E. coli isolate. In FIG. 4B, a bacterial lawn was created by inoculating a gentamicin resistant strain of Pseudomonas aeruginosa onto the agar plate prior to incubation with the filter paper containing M3A. The results demonstrate that the M3A antibiotic also inhibits the growth of the gentamicin resistant Pseudomonas strain, although not to as great an extent as the inhibition of the MDR E. coli isolate in FIG. 4A.

EXAMPLE 7

M3A Antibiotic Inhibition of Drug Resistant S. aureus and Enterococcus Isolates

Figure 5A:
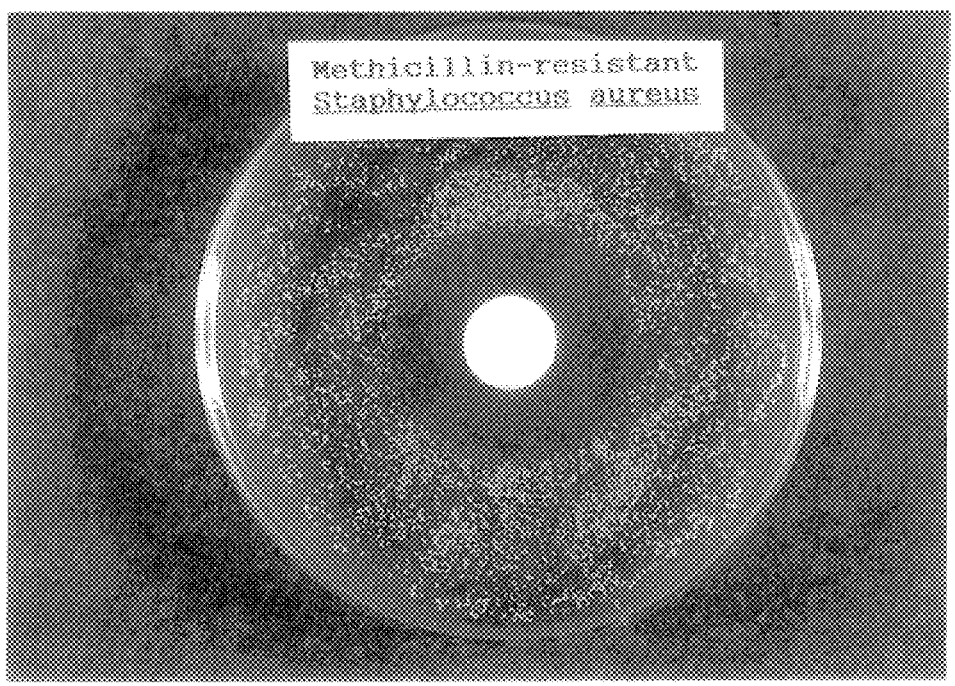
FIG. 5A is a photograph showing the inhibition of methicillin-resistant *Staphylococcus aureus* by the M3A antibiotic.
Figure 5B:
FIG. 5B is a photograph showing the the inhibition of vancomycin-resistant Enterococci by the M3A antibiotic.

In this experiment, agar plates were inoculated with either methicillin-resistant Staphylococcus aureus (FIG. 5A) or vancomycin-resistant Enterococci (FIG. 5B) and incubated with M3A, as described above in Example 5. Results demonstrate that the M3A antibiotic significantly inhibits the growth of both methicillin-resistant S. aureus and vancomycin-resistant Enterococci. Because both test organisms are common causes of nosocomial infections, the increase in antibiotic resistance among these strains represents a difficult treatment challenge.

EXAMPLE 8

Inhibition of Drug Resistant M. Avium Strains by the M3A Antibiotic

Mycobacterium avium is one of the causes of serious opportunistic infections in people with AIDS and other immune compromising conditions. In the following experiment, a multi-drug resistant strain of M. avium was plated on Middlebrook 7H10 agar, and allowed to form a bacterial lawn as described above. The M. avium isolate was resistant to the following drugs: ethambutol (5.0 µg/ml), rifampin (1.0 µg/ml), cycloserine (20 µg/ml), kanamycin (5.0 µg/ml), pyrazinamide (25 µg/ml), streptomycin (2.0 µg/ml), ofloxacin (5 µg/ml), ciprofloxacin (5, µg/ml), and isoniazid (1.0 µg/ml).

Figures 6A, 6B:
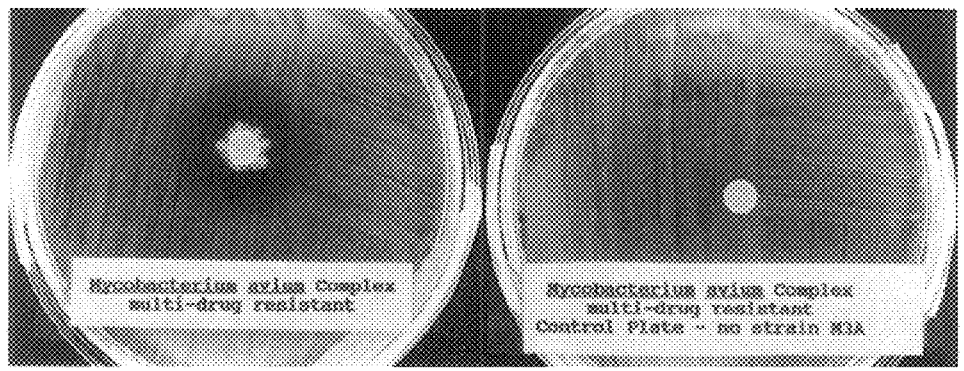
FIG. 6A is a photograph showing the inhibition of multi-drug resistant *Mycobacterium avium* by the M3A antibiotic.
FIG. 6B is a photograph of the control experiment, in which multi-drug resistant *M. avium* was incubated in the absence of strain M3A.

The effect of the MA3A antibiotic on M. avium was measured as previously described. Results showed significant inhibition in the growth of M. avium incubated with M3A (FIG. 6A), as compared to the control plate, incubated under identical conditions without strain M3A (FIG. 6B).

EXAMPLE 9

Inhibition of M. Tuberculosis by the M3A Antibiotic

Figures 7A, 7B:
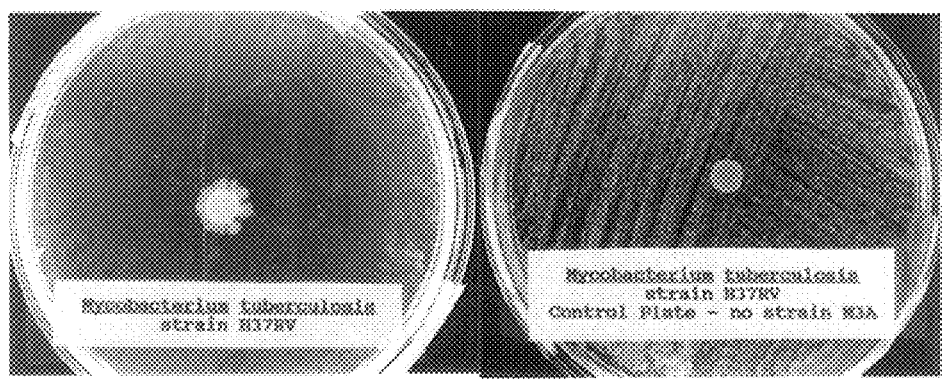
FIG. 7A is a photograph showing the inhibition of multi-drug resistant *Mycobacterium tuberculosis* by the M3A antibiotic.
FIG. 7B is a photograph of the control experiment, in which *M. tuberculosis* was incubated in the absence of strain M3A.

A bacterial lawn was plated with Mycobacterium tuberculosis strain H37RV and incubated with M3A, as described above. Results showed that the antibiotic elaborated by M3A strongly inhibits the resulting growth of M. tuberculosis (FIG. 7A), as compared to the control plate (FIG. 7B) incubated in the absence of strain M3A.

EXAMPLE 10

Method of Action of M3A Antibiotic Inhibition

Two methods were used to determine if the inhibitory effect of the M3A antibiotic was bactericidal (bacteria-killing) or bacteriostatic (bacterial-inhibiting) in nature. In the first, M3A was grown on filter paper disks and the disks placed on a lawn formed by the test organism. The resulting zone of inhibition was swabbed and the swab used to inoculate a fresh plate. If any growth of the test organism resulted, the M3A antibiotic's effect was bacteriostatic, as opposed to bactericidal.

In the second method, test bacteria were inoculated into M3A spent medium and incubated for 12 hours. Subsequently, an aliquot was plated out onto nutrient media. If no growth resulted, the antibiotic effect was bactericidal, while growth of the test organism indicated a bacteriostatic effect. Results of these experiments are summarized as follows:

| BACTERICIDAL | BACTERIOSTATIC |
|---|---|
| Gentamicin-resistant Pseudomonas aeruginosa | Proteus (strain 19661) |
| Vancomycin-resistant enterococci | Proteus (strain 19806) |
| E. coli (tetracycline-resistant) | Serratia marcescens |
| E. coli (ampicillin-resistant) | Staphylococcus aureus |
| Bacillus subtilis 6051 | Methicillin resistant S. aureus |
| Vibrio cholerae | |
| Salmonella typhimurium | |
| Micrococcus luteus | |
| S. salvarius 13419 | |
| Psedomonas aeruginosa | |

Although a preferred embodiment of the present invention has been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged, both in whole or in part.

What is claimed is:

1. A method for treating a bacterial infection in a patient, comprising the steps of:

administering to said patient a composition containing an anti-bacterial agent, said anti-bacterial agent comprising an antibiotic produced by culturing the M3A strain of *Alcaligenes faecalis* under aerobic conditions and at a temperature within a range of from 17° C. to 43° C. on a culture medium containing a citrate or succinate carbon source until sufficient antibotic activity is produced in said medium, wherein said antibiotic is administered in a therapeutically active dosage for a time effective to inhibit the growth of said bacterial infection in said patient.

2. A method according to claim 1, wherein said composition is administered via mucosal administration.

3. A method according to claim 1, wherein said composition is administered via parenteral administration.

4. A method according to claim 1, wherein said composition further comprises a pharmaceutically acceptable carrier.

5. A method according to claim 4, wherein said pharmaceutically acceptable carrier is chosen from the group consisting of physiological saline, dextrose, sterile water, and mixtures thereof.

6. A method according to claim 1, wherein said antibiotic is administered in a therapeutically active dosage, for a time effective to kill the bacteria in said bacterial infection.

7. A method according to claim 1, wherein said therapeutically active dosage is in the range of about 0.2 µg per kilogram of body weight per minute to about 200 g per kilogram of body weight per minute.

8. An anti-microbial composition for treating a bacterial infection in a human or animal patient, said composition comprising an antibiotic produced by the M3A strain of *Alcaligenes faecalis* bacterial and a pharmaceutically acceptable carrier, wherein said M3A strain of *Alcaligenes faecalis* bacteria is cultured under aerobic conditions and at a temperature within a range of from 17° C. to 43° C. on a culture medium containing a citrate or succinate carbon source until sufficient antibiotic activity is produced in said medium.

9. An antimicrobial composition as in claim 8, wherein said pharmaceutically acceptable carrier is chosen from the group consisting of physiological saline, dextrose, sterile water, and mixtures thereof.

10. An antimicrobial composition as in claim 8, wherein said composition is in the form of a sterile injectable formulation.

11. An antimicrobial composition as in claim 8, wherein said composition is formulated as a sterile solid, and said sterile solid is chosen from the group consisting of tablets, capsules, suppositories, and liquids.

12. An antimicrobial composition as in claim 8, wherein said composition is formulated to deliver a therapeutically active dosage in the range of about 0.2 µg per kilogram of body weight per minute to about 200 g per kilogram of body weight per minute.

* * * * *